United States Patent [19]

Scheuble et al.

[11] Patent Number: 4,970,022
[45] Date of Patent: Nov. 13, 1990

[54] LIQUID-CRYSTALLINE MUSTARD OILS

[75] Inventors: Bernhard Scheuble, Yokohama, Japan; Rudolf Eidenschink, Mühltal, Fed. Rep. of Germany; Joachim Krause, Dieburg, Fed. Rep. of Germany; Eike Poetsch, Mühltal, Fed. Rep. of Germany; Andreas Wächtler, Griesheim, Fed. Rep. of Germany

[73] Assignee: Merck Patent Gesellschaft mit beschrankter Haftung, Darmstadt, Fed. Rep. of Germany

[21] Appl. No.: 110,756

[22] PCT Filed: Dec. 6, 1986

[86] PCT No.: PCT/EP86/00720
§ 371 Date: Aug. 19, 1987
§ 102(e) Date: Aug. 19, 1987

[87] PCT Pub. No.: WO87/03870
PCT Pub. Date: Jul. 2, 1987

[30] Foreign Application Priority Data

Dec. 20, 1985 [DE] Fed. Rep. of Germany ....... 3545345

[51] Int. Cl.$^5$ ................ C07D 403/00; C07D 239/02; C07D 211/00; C07D 211/32; C07D 401/00; C09K 19/34; C07C 331/00; C07C 291/00
[52] U.S. Cl. .............................. 252/299.61; 544/335; 544/242; 544/357; 544/406; 544/410; 544/336; 544/408; 544/238; 544/240; 544/239; 544/224; 544/295; 544/296; 544/298; 544/316; 546/186; 546/189; 546/190; 546/191; 546/205; 546/206; 546/216; 546/217; 546/218; 546/219; 546/220; 546/221; 546/222; 546/225; 546/226; 546/227; 546/228; 546/229; 546/230; 546/232; 546/235; 252/299.6; 252/299.62; 252/299.63; 252/299.65; 252/299.68; 252/299.66; 252/299.64; 252/299.67; 350/350 R; 350/350 S; 558/17; 534/567; 534/566

[58] Field of Search ........... 252/299.6, 299.61, 299.62, 252/299.63, 299.65, 299.68, 299.66, 299.64, 299.67; 350/250 R, 250 S; 558/17; 534/567, 566; 544/238, 240, 239, 224, 295, 296, 298, 316, 335, 242, 357, 406, 408, 410, 336; 546/186, 189, 190, 191, 205, 206, 216, 217, 218, 219, 220, 221, 222, 225, 226, 227, 228, 229, 230, 232, 235

[56] References Cited

U.S. PATENT DOCUMENTS

| 4,528,116 | 7/1965 | Dabrowski et al. | 252/299.63 |
| 4,621,901 | 11/1986 | Petrzilka et al. | 252/299.61 |
| 4,676,924 | 6/1987 | Dabrowski et al. | 252/299.61 |
| 4,709,030 | 11/1987 | Petrzilka et al. | 252/299.6 |
| 4,770,503 | 9/1988 | Buchecker et al. | 252/299.63 |
| 4,849,130 | 7/1989 | Dabrowski et al. | 252/299.61 |

FOREIGN PATENT DOCUMENTS

| 169327 | 1/1986 | European Pat. Off. | 252/299.61 |
| 195974 | 10/1986 | European Pat. Off. | 252/299.63 |
| 227004 | 7/1987 | European Pat. Off. | 252/299.63 |
| 3500909 | 7/1986 | Fed. Rep. of Germany | 252/299.61 |
| 60-136555 | 7/1985 | Japan | 252/299.63 |
| 60-146868 | 8/1985 | Japan | 252/299.63 |
| 60-204781 | 10/1985 | Japan | 252/299.61 |
| 60-222458 | 11/1985 | Japan | 252/299.63 |
| 61-43172 | 3/1986 | Japan | 252/299.61 |
| 61-189263 | 8/1986 | Japan | 252/299.63 |
| 8603769 | 7/1986 | PCT Int'l Appl. | 252/299.61 |
| 8605799 | 10/1986 | PCT Int'l Appl. | 252/299.61 |

OTHER PUBLICATIONS van der Veen, J., J. Phys. (Paris), Colloq (3), pp. 13–15, (1976).
Dabrowski, R., et al., Mol. Cryst. Liq. Cryst., vol. 107, pp. 411–443, (6/84).
Dabrowski, R., et al., J. De Physique, vol. 45, pp. 1213–1222, (Jul. 1984).

Primary Examiner—Teddy S. Gron
Assistant Examiner—Richard Treanor
Attorney, Agent, or Firm—Millen, White & Zelano

[57] ABSTRACT

Mustard oils of the formula I

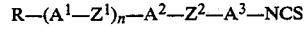

in which $A^1$, $A^2$, $A^3$, R, $Z^1$, $Z^2$ and n have the meaning specified in Claim 1 can be used as components of liquid-crystalline phases.

11 Claims, No Drawings

LIQUID-CRYSTALLINE MUSTARD OILS

Liquid-crystalline mustard oils The invention relates to mustard oils of the formula I, $$R-(A^1-Z^1)_n-A^2-Z^2-A^3-NCS \qquad (I)$$

in which

R is H or alkyl of 1-15 C atoms, in which one or two non-adjacent $CH_2$ groups can be replaced by —CH=CH—, —O—, —CO—, —O—CO— and/or —CO—O—, $A^1$ and $A^2$ are each an unsubstituted or monosubstituted or polysubstituted 1,4-cyclohexylene group, a piperidine-1,4-diyl or 1,4-bicyclo[2.2.2]octylene group or a 1,4-phenylene group which is unsubstituted or substituted by one or two F and/or Cl atoms and/or $CH_3$ groups and/or CN groups and in which one or two CH groups can also be replaced by N, $A^3$ is an unsubstituted or monosubstituted or polysubstituted 1,4-cyclohexylene group or a 1,4-phenylene group which is unsubstituted or substituted by one or two F and/or Cl atoms and/or $CH_3$ groups and/or $CF_3$ groups and/or CN groups, $Z^1$ and $Z^2$ are each —CO—O—, —O—CO—, —O—, —$CH_2$—, —CHCN—$CH_2$—, —$CH_2$—CHCN—, —CH=CH—, —$OCH_2$—, —$CH_2O$—, —CH=N—, —N=CH—, —NO=N—, —N=NO— or a single bond, n is 0, 1 or 2, with the proviso that, when $A^3$ is an unsubstituted 1,4-phenylene group, n is 2 or $Z^2$ is no single bond or $A^2$-$Z^2$ is Pyr or Cy-$CH_2CH_2$- and in the case of $Z^2$=—CO—O—, —$(A^1-Z^1)_n$—$A^2$— is not

or 1,4-phenylene.

For simplicity, in what follows Cy is a 1,4-cyclohexylene group, Bi a bicyclo[2.2.2]octylene-1,4-diyl group, Pip a piperidine-1,4-diyl group, Phe a 1,4-phenylene group, Pym a pyrimidine-2,5-diyl group, Pyr a pyridine-2,5-diyl group and Pyz a pyrazine-2,5-diyl group, where Cy and/or Phe and/or Pyr and/or Pyz can be unsubstituted or substituted by one or two F and/or Cl atoms and/or $CH_3$ groups and/or $CF_3$ groups and/or CN groups.

The compounds of the formula I can be used as components of liquid-crystalline phases, in particular for displays which are based on the principle of the twisted cell, the guest-host effect, the effect of the deformation of aligned phases or the effect of dynamic scattering.

The invention has for its object to find new stable liquid-crystalline or mesogenic compounds which are suitable for use as components of liquid-crystalline phases and in particular have a comparatively low viscosity and a reduced tendency to form associates.

EP No. 0,126,883 discloses liquid-crystalline mustard oils which contain a trans-cyclohexylphenyl group.

It was found, then, that compounds of the formula I are highly suitable for use as components of liquid-crystalline phases. In particular they have comparatively low viscosities and no or only little tendency to form molecular associates. They can be used to obtain stable liquid-crystalline phases having a wide mesophase range and advantageous optical and dielectric anisotropy values.

Making available compounds of the formula I, in addition, very generally serves to appreciably widen the range of liquid-crystalline substances which, from various application aspects, are suitable for preparing liquid-crystalline mixtures.

The compounds of the formula I have a wide application range. Depending on the choice of substituents, these compounds can serve as base materials of which liquid-crystalline phases are predominantly composed; but compounds of the formula I can also be added to liquid-crystalline base materials of other classes of compounds, for example in order to influence the dielectric and/or optical anisotropy of such a dielectric and/or to reduce the threshold voltage thereof and/or the viscosity thereof.

The compounds of the formula I are colourless in the pure state and form liquid-crystalline mesophases in a temperature range suitable for electro-optical use. They are stable chemically, thermally and to light.

The invention thus provides the compounds of the formula I and a process for preparing the compounds of the formula I according to claim 1, characterized in that an appropriate amine is treated with thiophosgene, or in that an appropriate amine is converted with carbon disulfide into a dithiocarbamate and the latter is treated with hydrogen peroxide or a chlorocarbonic acid ester, or in that an appropriate halide of the formula I in which $A^3$ is a cyclohexylene group is reacted with a salt of thiocyanic acid, or in that a compound which otherwise conforms to the formula I but contains one or more reducible groups and/or C-C bonds in place of H atoms is treated with a reducing agent, or in that, to prepare compounds of the formula I in which $A^3$ is a 1,4-phenylene group which is substituted by one or two F and/or Cl atoms and/or CN groups, the diazonium group in an appropriate diazonium salt is replaced by F, Cl or CN, or in that, to prepare benzotrifluorides of the formula I in which $A^3$ is a 1,4-phenylene group which is substituted by one or two $CF_3$ groups, an appropriate carboxylic acid or the anhydride thereof is reacted with sulfur tetrafluoride, or in that, to prepare esters of the formula I (in which $Z^1$ and/or $Z^2$ are —CO—O— or —O—CO— and/or R contains a carboxyl group), an appropriate carboxylic acid or one of the reactive derivatives thereof is reacted with an appropriate alcohol or a reactive derivative thereof, or in that, to prepare nitriles of the formula I (in which $A^1$ and/or $A^2$ and/or $A^3$ is substituted by at least one CN group), an appropriate carboxamide is dehydrated or an appropriate carbonyl halide is reacted with sulfamide, and/or in that if desired a chlorine or bromine compound of the formula I (in which $A^1$ and/or $A^2$ and/or $A^3$ is substituted by at least one chlorine or bromine atom) is reacted with a cyanide, or in that, to prepare ethers of the formula I (in which $R^3$ is an alkoxy group and/or $Z^1$ and/or $Z^2$ is an —$OCH_2$— or —$CH_2O$— group), an appropriate hydroxy compound is etherified.

The invention further provides the use of compounds of the formula I as components of liquid-crystalline phases. The invention also provides liquid-crystalline phases which contain at least one compound of the formula I and liquid crystal display elements, in particular electro-optical display elements, which contain such phases.

Heretofore and hereinafter, R, $A^1$, $A^2$, $A^3$, $Z^1$, $Z^2$ and n have the specified meaning, unless expressly stated otherwise.

The compounds of the formula I correspondingly comprise compounds having two rings of the formula I a:

$$R—A^2—Z^2—A^3—NCS \qquad \text{I a}$$

compounds having three rings of the formulae I b and I c:

$$R—A^1—A^2—Z^2—A^3—NCS \qquad \text{I b}$$
$$R—A^1—Z^1—A^2—Z^2—A^3—NCS \qquad \text{I c}$$

and compounds having four rings of the formulae Id to I g:

$$R—A^1—A^1—A^2—Z^2—A^3—NCS \qquad \text{I d}$$
$$R—A^1—Z^1—A^1—A^2—Z^2—A^3—NCS \qquad \text{I e}$$
$$R—A^1—A^1—Z^1—A^2—Z^2—A^3—NCS \qquad \text{I f}$$
$$R—A^1—Z^1—A^1—Z^1—A^2—Z^2—A^3—NCS \qquad \text{I g}$$

as well as compounds having five rings of the formulae I h to I o:

$$R—A^1—A^1—A^1—A^2—Z^2—A^3—NCS \qquad \text{I h}$$
$$R—A^1—Z^1—A^1—A^1—A^2—Z^2—A^3—NCS \qquad \text{I i}$$
$$R—A^1—A^1—Z^1—A^1—A^2—Z^2—A^3—NCS \qquad \text{I j}$$
$$R—A^1—A^1—A^1—Z^1—A^2—Z^2—A^3—NCS \qquad \text{I k}$$
$$R—A^1—Z^1—A^1—Z^1—A^1—A^2 Z^2—A^3—NCS \qquad \text{I l}$$
$$R—A^1—Z^1—A^1—A^1—Z^1—A^2—Z^2—A^3—NCS \qquad \text{I m}$$
$$R—A^1—A^1—Z^1—A^1—Z^1—A^2—Z^2—A^3—NCS \qquad \text{I n}$$
$$R—A^1—Z^1—A^1—Z^1—A^1—Z^1—A^2—Z^2—A^3—NCS \qquad \text{I o}$$

In the compounds of the preceding and following formulae, R is preferably alkyl and also alkoxy.

$A^1$, $A^2$ and $A^3$ are preferably Cy, Phe, Pym or Pyr; preferably the compounds of the formula I contain not more than one of the radicals By, Pyd, Pym, Pyr or Pyz.

$Z^1$ and $Z^2$ are preferably single bonds, and secondarily preferably —CO—O—, —O—CO— or —CH$_2$CH$_2$—groups.

An alkyl radical and/or an alkoxy radical R can be straight-chain or branched. Preferably it is straight-chain, has 2, 3, 4, 5, 6 or 7 C atoms and accordingly preferably is ethyl, propyl, butyl, pentyl, hexyl, heptyl, ethoxy, propoxy, butoxy, pentoxy, hexoxy or heptoxy, and also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

An alkyl radical R in which a CH2 group has been replaced by -CH=CH- can be straight-chain or branched. Preferably it is straight-chain and has 2 to 10 carbon atoms. It accordingly is in particular vinyl, prop-1- or prop-2-enyl, but-1-, -2- or but-3-enyl, pent-1-, -2-, -3-or pent-4-enyl, hex-1-, -2-, -3-, -4- or hex-5-enyl, hept-1-, -2-, -3-, -4-, -5- or hept-6-enyl, oct-1-, -2-, -3-, -4-, -5-, -6- or oct-7-enyl, non-1-, -2-, -3-, -4-, -5-, -6-, -7- or non-8-enyl, dec-1-, -2-, -3-, -4-, -5-, -6-, -7-, -8- or dec-9-enyl.

Compounds of the formulae I having branched wing groups R can occasionally be of importance on account of better solubility in the customary liquid-crystalline base materials, but in particular for use as chiral dopants, if they are optically active. Smectic compounds of this type are suitable for use as components for ferroelectric materials.

Branched groups of this type generally contain not more than one chain branching. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methlheptoxy.

Formula I covers not only the racemates of these compounds but also the optical antipodes and mixtures thereof. Of the compounds of the formula I and I a to I o, preference is given to those in which at least one of the radicals present therein has one of the indicated preferred meanings.

Particularly preferred smaller groups of compounds are those of the formula I 1 to I 20 in which Phe is 1,4-phenylene, Cy is 1,4-cyclohexylene and Phef is 1,4-phenylene substituted in the 2- or 3-position by fluorine:

| | |
|---|---|
| R—Cy—Cy—NCS | I 1 |
| R—Pym—Phe—NCS | I 2 |
| R—Pym—PheF—NCS | I 3 |
| R—Cy—COO—PheF—NCS | I 4 |
| R—Cy—Phe—Cy—NCS | I 5 |
| R—Cy—Pym—Phe—NCS | I 6 |
| R—Cy—CH$_2$CH$_2$—Phe—NCS | I 7 |
| R—Pym—CH$_2$CH$_2$—Phe—NCS | I 8 |
| R—Cy—CH$_2$CH$_2$—Cy—Phe—NCS | I 9 |
| R—Cy—CH$_2$CH$_2$—Cy—COO—Phe—NCS | I 10 |
| R—Cy—Phe—Phe—NCS | I 11 |
| R—Cy—PheF—Phe—NCS | I 12 |
| R—Cy—Phe—Phe—Cy—NCS | I 13 |
| R—Cy—PheF—Phe—Cy—NCS | I 14 |
| R—Pyr—Phe—NCS | I 15 |
| R—Cy—Pyr—Phe—NCS | I 16 |
| R—Phe—Pyr—Phe—NCS | I 17 |
| R—Cy—Cy—Cy—Phe—NCS | I 18 |
| R—Cy—Cy—CH$_2$CH$_2$—Phe—NCS | I 19 |

R—Cy—CH$_2$CH$_2$—Cy—Phe—NCS    I 20

In the compounds of the formula I, preference is given to those stereoisomers where the rings Cy and Pip are trans-1,4-disubstituted. Those of the aforementioned formulae which contain one or more groups Pip, Pyd, Pym, Pyr and/or Pyz cover in each case the two 2,5- (Pym, Pyr) and 1,4-positional isomers (Pip).

In the compounds of the formula I in which A$^1$ is a Pyd, Pym, Pyr or Pyz ring which is substituted in the 2-position by R, R is preferably alkyl.

Particular preference is given to compounds of the formula I in which R is in each case straight-chain or at most singly branched alkyl or alkoxy of 1-12, in particular 2-10, C atoms.

Particular preference is given to the following minor groups of compounds in which Pym is pyrimidine-2,5-diyl, Phe is 1,4-phenylene, Cy is 1,4-cyclohexylene and PheF is 1,4-phenylene substituted in the 2- or 3-position by fluorine.

Alkyl is preferably a straight-chain methyl, ethyl, propyl, butyl, pentyl, hexyl, heptyl, octyl, nonyl or decyl; oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

| | |
|---|---|
| I. | Alkyl-Cy-Cy-NCS |
| | Oxaalkyl-Cy-Cy-NCS |
| II. | Alkyl-Pym-Phe-NCS |
| | Alkoxycarbonyl-Pym-Phe-NCS |
| | Alkyl-Pym-Phe-2F,NCS |
| | Alkyl-Pym-Phe-3F,NCS |
| | Alkoxycarbonyl-Pym-Phe-2F,NCS |
| | Alkoxycarbonyl-Pym-Phe-3F,NCS |
| III. | Alkyl-Cy-COO-Phe-2F,NCS |
| | Alkyl-Cy-COO-Phe-3F,NCS |
| IV. | Alkyl-Cy-Phe-Cy-NCS |
| V. | Alkyl-Cy-Pym-Phe-NCS |
| | Alkoxycarbonyl-Cy-Pym-Phe-NCS |
| VI. | Alkyl-Pym-CH$_2$CH$_2$-Phe-NCS |
| | Oxaalkyl-Pym-CH$_2$CH$_2$-Phe-NCS |
| VII. | Alkyl-Cy-CH$_2$CH$_2$-Phe-NCS |
| | Alkoxycarbonyl-Cy-CH$_2$CH$_2$-Phe-NCS |
| VIII. | Alkyl-Cy-CH$_2$CH$_2$-Cy-Phe-NCS |
| | Alkoxycarbonyl-Cy-CH$_2$CH$_2$-Cy-Phe-NCS |
| | Alkyl-Cy-CH$_2$CH$_2$-Cy-Phe-2F,NCS |
| | Alkyl-Cy-CH$_2$CH$_2$-Cy-Phe-3F,NCS |
| | Alkoxycarbonyl-Cy-CH$_2$CH$_2$-Cy-Phe-2F,NCS |
| | Alkoxycarbonyl-Cy-CH$_2$CH$_2$-Cy-Phe-3F,NCS |
| IX. | Alkyl-Cy-CH$_2$CH$_2$-Cy-COO-Phe-NCS |
| X. | Alkyl-Cy-Phe-Phe-NCS |
| | Oxaalkyl-Cy-Phe-Phe-NCS |
| | Alkyl-Cy-(Phe-2F)-Phe-NCS |
| | Alkyl-Cy-(Phe-3F)-Phe-NCS |
| XI. | Alkyl-Cy-Phe-Phe-Cy-NCS |
| | Alkyl-Cy-(Phe-2F)-Cy-NCS |
| | Alkyl-Cy-(Phe-3F)-Cy-NCS |
| XII. | Alkyl-Cy-Pyr-Phe-NCS |
| | Alkyl-Phe-Pyr-Phe-NCS |
| XIII. | Alkyl-Pyr-Phe-NCS |
| XIV. | Alkyl-Cy-Cy-CH$_2$CH$_2$-Phe-NCS |
| XV. | Alkyl-Cy-Cy-Cy-Phe-NCS |

The compounds of the formula I are prepared by methods known per se as described in the literature (for example in the standard works such as Houben-Weyl, Methoden der organischen Chemie [Methods of Organic Chemistry], Georg-Thieme-Verlag, Stuttgart Volume IX, pages 867 ff.), under reaction conditions which are known and suitable for the reactions mentioned. In this it is also possible to make use of variants known per se which are not further explained here.

The starting materials can :f desired also be formed in situ by not isolating them out of the reaction mixture but immediately reacting them further to give the compounds of the formula I.

For instance, the compounds of the formula I can be prepared by reducing a compound which otherwise conforms to the formula I but contains one or more reducible groups and/or C-C bonds in place of H atoms.

Preferred reducible groups are carbonyl groups, in particular keto groups, and also, for example, free or esterified hydroxyl groups or aromatically bonded halogen atoms. Preferred starting materials for the reduction conform to the formula I, but can contain in place of a cyclohexane ring a cyclohexene ring or cyclohexanone ring and/or in place of a —CH$_2$CH$_2$— group a —CH=CH— group and/or in place of a —CH$_2$— group a —CO— group and/or in place of an H atom a free or functionally (for example in the form of the p-toluenesulfonate thereof) modified OH group.

The reduction can be effected for example by catalytic hydrogenation at temperatures at between about 0° and about 200° and pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are preferably noble metals such as Pt or Pd, which can be used in the form of oxides (for example PtO$_2$, PdO), on a carrier (for example Pd on carbon, calcium carbonate or strontium carbonate) or in finely divided form.

Ketones can also be reduced by the methods of Clemmensen (using zinc, amalgamated zinc or tin and hydrochloric acid, preferably in aqueous alcoholic solution or in heterogeneous phase with water/toluene at temperatures between about 80° and 120°) or Wolff-Kishner (with hydrazine, preferably in the presence of alkali such as KOH or NaOH in a high-boiling solvent such as diethylene glycol or triethylene glycol at temperatures between about 100° and 200°) to the corresponding compounds of the formula I which contain alkyl groups and/or —CH$_2$CH$_2$— bridges.

Reductions with complex hydrides are also possible. For example, arylsulfonyloxy groups can be reductively removed using LiAlH$_4$, in particular p-toluenesulfonyloxymethyl groups can be reduced to methyl groups, preferably in an inert solvent such as diethyl ether or THF at temperatures between about 0° and 100°. Double bonds can be hydrogenated with NaBH$_4$ or tributyltin hydride in methanol.

Esters of the formula I can also be obtained by esterifying corresponding carboxylic acids (or reactive derivatives thereof) with alcohols or phenols (or reactive derivatives thereof).

The corresponding carboxylic acids and alcohols or phenols are known or can be prepared analogously to known processes.

Suitable reactive derivatives of the carboxylic acids mentioned are in particular the acid halides, especially the chlorides and bromides, and further the anhydrides, including, for example, mixed anhydrides, azides or esters, in particular alkyl esters having 1 - 4 C atoms in the alkyl group.

Suitable reactive derivatives of the alcohols and phenols mentioned are in particular the corresponding metal alcoholates or phenolates, preferably of an alkali metal such as sodium or potassium.

The esterification is advantageously carried out in the presence of an inert solvent. Highly suitable are in particular ethers such as diethyl ether, di-n-butyl ether, THF, dioxane or anisole, ketones such as acetone, butanone or cyclohexanone, amides such as DMF or hexamethylphosphoramide, hydrocarbons such as benzene, toluene or xylene, halohydrocarbons such as carbon tetrachloride or tetrachloroethylene and sulfoxides such as dimethyl sulfoxide or sulfolane. Water-immiscible solvents can at the same time advantageously be used for removing, by azeotropic distillation, the water formed in the course of the esterification. Occasionally it can also be possible to use an excess of an organic base, for example pyridine, quinoline or triethylamine, as the solvent for the esterification. The esterification can also be carried out in the absence of a solvent, for example by simply heating the components in the presence of sodium acetate. The reaction temperature is customarily between $-50°$ and $+250°$, preferably between $-20°$ and $+80°$. At these temperatures the esterification reactions are generally complete within 15 minutes to 48 hours.

In detail, the reaction conditions for the esterification largely depend on the nature of the starting materials used. For instance, a free carboxylic acid is generally reacted with a free alcohol or phenol in the presence of a strong acid, for example a mineral acid such as hydrochloric acid or sulfuric acid. A preferred way of carrying out the reaction is to react an acid anhydride or in particular an acid chloride with an alcohol preferably in a basic medium, suitable bases being in particular alkali metal hydroxides such as sodium hydroxide or potassium hydroxide, alkali metal carbonates or hydrogencarbonates such as sodium carbonate, sodium hydrogencarbonate, potassium carbonate or potassium hydrogencarbonate, alkali metal acetates such as sodium acetate or potassium acetate, alkaline earth metal hydroxides such as calcium hydroxide or organic bases such as triethylamine, pyridine, lutidine, collidine or quinoline. A further preferred embodiment of the esterification comprises first converting the alcohol or phenol into the sodium or potassium alcoholate or phenolate, for example by treatment with ethanolic sodium hydroxide or potassium hydroxide solution, isolating the alcoholate or phenolate and suspending it together with sodium hydrogencarbonate or potassium carbonate with stirring in acetone or diethyl ether, and treating this suspension with a solution of the acid chloride or anhydride in diethyl ether, acetone or DMF, preferably at temperatures between about $-25°$ and $20°$.

To prepare nitriles of the formula I (in which $A^1$, $A^2$ and/or $A^3$ is substituted by at least one CN group), appropriate acid amides, for example those in which the CN radical has been replaced by a $CONH_2$ group, can be dehydrated. The amides are obtainable for example from appropriate esters or acid halides by reaction with ammonia. Suitable water-eliminating agents are for example inorganic acid chlorides such as $SOCl_2$, $PCl_3$, $PCl_5$, $POCl_3$, $SO_2Cl_2$, $COCl_2$, and further $P_2O_5$, $P_2S_5$, $AlCl_3$ (for example as a double compound with NaCl), aromatic sulfonic acids and sulfonyl halides. The dehydration can be carried out in the presence or absence of an inert solvent at temperatures between about $0°$ and $150°$; examples of suitable solvents are bases such as pyridine or triethylamine, aromatic hydrocarbons such as benzene, toluene or xylene or amides such as DMF.

To prepare the abovementioned nitriles of the formula I, it is also possible to react appropriate acid halides, preferably the chlorides, with sulfamide, preferably in an inert solvent such as tetramethylene sulfone at temperatures between about $80°$ and $150°$, preferably at $120°$. After customary working-up the nitriles can be isolated directly.

Ethers of the formula I (in which R is an alkoxy group and/or in which $Z^1$ and/or $Z^2$ is a $—OCH_2—$ or a $—CH_2O—$ group) are obtainable by etherifying appropriate hydroxy compounds, preferably appropriate phenols, the hydroxy compound preferably being first converted into a corresponding metal derivative, for example by treatment with NaH, $NaNH_2$, NaOH, KOH, $Na_2CO_3$ or $K_2CO_3$ in the corresponding alkali metal alcoholate or alkali metal phenolate. The latter can then be reacted with the corresponding alkyl halide or sulfonate or dialkyl sulfate, preferably in an inert solvent such as acetone, 1,2-dimethoxyethane, DMF or dimethyl sulfoxide or even in an excess of aqueous or aqueous alcoholic NaOH or KOH at temperatures between about $20°$ and $100°$.

To prepare nitriles of the formula I (in which $A^1$, $A^2$ and/or $A^3$ is substituted by at least one CN group) it is also possible to react corresponding chlorine or bromine compounds of the formula I (in which $A^1$ and/or $A^2$ and/or $A^3$ is substituted by at least one Cl or Br atom) with a cyanide, preferably with a metal cyanide such as NaCN, KCN or $Cu_2(CN)_2$, for example in the presence of pyridine in an inert solvent such as DMF or N-methylpyrrolidone at temperatures between $20°$ or $200°$.

Compounds of the formula I in which $A^1$, $A^2$ and/or $A^3$ is substituted by at least one F or Cl atom and/or a CN group can also be obtained from the corresponding diazonium salts by replacing the diazonium group with a fluorine or chlorine atom or with a CN group, for example by the methods of Schiemann or Sandmeyer.

The diazonium salts are preparable for example by nitrating compounds which conform to the formula I but contain a hydrogen atom in place of the radical $NO_2$, reducing to the corresponding amines and diazotizing, for example with $NaNO_2$ or $KNO_2$ in aqueous solution at temperatures between about $-10°$ and $+10°$.

To replace the diazonium group by fluorine, it is possible to diazotize in anhydrous hydrochloric acid and then to heat, or to react with tetrafluoroboric acid to give the diazonium tetrafluoroborates, which are then thermally decomposed.

Replacement for Cl or CN is preferably possible by reacting the aqueous diazonium salt solution with $Cu_2Cl_2$ or $Cu_2(CN)_2$ by the method of Sandmeyer.

Compounds of the formula I in which $A^1$, $A^2$ and/or $A^3$ is substituted by at least one $CF_3$ group can be obtained from carboxylic acids or derivatives thereof, for example acid halides or anhydrides, with sulfur tetrafluoride at elevated temperature.

Particularly advantageously, compounds of the formula I are obtained by reacting corresponding amines with thiophosgene by the method described for example in German Patent No. 1,117,257.

Such amines of the formula I, which have an amino group in place of the NCS group, are known or can be obtained by known methods. For instance, nitro compounds or oximes can be reduced to amino compounds using, for example, hydrogen and metal catalysis or by means of complex hydrides.

It is also possible to react aliphatic or aromatic halogen compounds, such as, for example, chlorides, bromides and iodides, with ammonia or an ammonia equivalent such as, for example, phthalimide potassium with metal salt catalysis, in particular in the presence of copper and/or salts thereof, to form amines.

The reactants for the reduction are made to react with one another without solvent or preferably in the presence of an inert solvent.

Suitable diluents are preferably ethers such as diethyl ether, dibutyl ether, tetrahydrofuran, dioxane, amides such as dimethylformamide, hexamethylphosphoramide, hydrocarbons such as hexane, cyclohexane, benzene, toluene, xylene, halohydrocarbons such as dichloromethane, chloroform, carbon tetrachloride, tetrachloroethylene, sulfoxides such as dimethyl sulfoxide, sulfolane and other organic solvents such as acetonitrile and nitromethane. Even water or mixtures of these solvents with water are suitable for the above reaction. The reaction temperatures are between −20° and +100°, preferably between 0° and 50°. At these temperatures the reactions are generally complete within 30 minutes to 24 hours.

In a further advantageous process, corresponding halides of the formula I in which $A^3$ is a cyclohexylene group are reacted with a salt of thiocyanic acid. Suitable salts for this purpose are for example ammonium thiocyanate, sodium thiocyanate and potassium thiocyanate. The reaction is advantageously carried out in the presence of an inert apolar solvent. Highly suitable are in particular hydrocarbons such as hexane, petroleum ether, ligroin, cyclohexane, benzene, toluene and xylene. The reaction temperatures are between 0° and 150°, preferably between 20° and 100°. At these temperatures the reactions are generally complete within 1 to 60 hours.

Finally, it is also possible to convert amines of the formula I which have an amino group in place of the NCS group with carbon disulfide into a dithiocarbamate, which is then converted by means of various reagents to the mustard oils according to the invention of the formula I. Reagents suitable for carrying out this reaction sequence are, for example, hydrogen peroxide (cf. DE 2,105,473), chlorocyan (DE 2,603,508), cyanuric chloride (DE 1,935,302), chlorocarbonic acid esters (DE 1,178,423), alkali metal hypochlorite or alkali metal chlorite (DE 952,083), phosgene (DE 1,068,250) and heavy metal salts (Dains et al., Org. Synth. Coll. Vol. 1 (1964) 447).

The preparation of the dithiocarbamates from the amino compounds conforming to the formula I and carbon disulfide is preferably effected in an inert solvent in the presence of an amine. Suitable solvents are for example hydrocarbons such as hexane, petroleum ether, ligroin, cyclohexane, benzene, toluene and xylene. Preferred amines are tertiary amines such as, for example, pyridine, triethylamine or ethyldiisopropylamine. The ammonium dithiocarbamates obtained can be isolated, for example, by centrifuging or filtration, but they can also be further reacted in situ to give mustard oils of the formula I.

The reaction temperatures to prepare the dithiocarbamates are between −20° and +100°, preferably between 0° and 40°. At these temperatures the reactions are generally complete within 1 to 24 hours.

To convert the ammonium dithiocarbamates, the preferred reaction is with chlorocarbonic acid esters or hydrogen peroxide.

The isolated or in situ generated ammonium dithiocarbamates can be made to react preferably in the presence of a suitable solvent such as, for example, ethers such as diethyl ether, tetrahydrofuran, dioxane and halohydrocarbons such as dichloromethane, chloroform, carbon tetrachloride, 1,2-dichloroethane in the case of chlorocarbonic acid esters or water, formic acid, acetic acid in the case of hydrogen peroxide. At reaction temperatures of −20° to 100°, preferably between 0° and 80°, the reactions are generally complete within 1 to 24 hours.

A particularly suitable way of preparing mustard oils of the formula I is the reaction of suitable amines with carbon disulfide and triethylamine to give triethylammonium dithiocarbamates and conversion of the latter into mustard oils by treatment with alkyl chlorocarbonates or hydrogen peroxide.

A base of the formula I can be converted with an acid into the corresponding acid addition salt. This reaction can be effected with inorganic acids, for example sulfuric acid, nitric acid, halohydric acids such as hydrochloric acid or hydrobromic acid, phosphoric acids such as orthophosphoric acid, sulfamic acid, and also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalene monosulfonic and naphthalene disulfonic acids, laurylsulfuric acid.

It is conversely possible to treat an acid addition salt of a compound of the formula I with a base, for example with a strong inorganic base such as KOH or NaOH, to free the base of the formula I.

The liquid-crystalline phases according to the invention consist of 2 to 25, preferably 3 to 15, components, including at least one compound of the formula I. The other constituents are preferably selected from the nematic or nematogenic substances, in particular the known substances, of the classes of the azoxybenzenes, benzylideneanilines, biphenyls, terphenyls, phenyl or cyclohexyl benzoates, phenyl or cyclohexyl cyclohexanecarboxylates, phenyl cyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidine, cyclohexylpyrimidine, phenyldioxane, cyclohexyldioxane, phenyldithiane, cyclohexyldithiane, 1,2-bisphenylethanes, 1,2-biscyclohexylethanes, 1-phenyl-2-cyclohexylethanes, optionally halogenated stilbenes, benzyl phenyl ethers, tolanes and substituted cinnamic acids.

The most important compounds for use as constituents of such liquid-crystalline phases can be characterized by the formula II

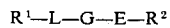  II in which L and E are each a carbocyclic or heterocyclic ring system from the group comprising 1,4-disubstituted benzene and cyclcohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or —CN, and $R^1$ and $R^2$ are alkyl, alkoxy, alkanoyloxy or alkoxycarbonyloxy having up to 18, preferably up to 8, carbon atoms, or one of these radicals can also be CN, $NO_2$, $CF_3$, F, Cl or Br.

With most of these compounds, $R^1$ and $R^2$ are different from each other, one of these radicals usually being an alkyl or alkoxy group. But other variants of the proposed substituents are also customary. Many such substances or even mixtures thereof are commercially available. All these substances are preparable by literature methods.

The liquid-crystalline phases according to the invention contain about 0.1 to 99%, preferably 10 to 95%, of one or more compounds of the formula I. Preference is further given to liquid-crystalline phases which contain 0.1–50%, in particular 0.5–30%, of one or more compounds of the formula I. Even isotropic compounds of the formula I can be present in the phases according to the invention.

The liquid-crystalline phases according to the invention are prepared in a conventional manner. In general, the components are dissolved in one another, preferably at elevated temperature.

By means of suitable additives the liquid-crystalline phases according to the invention can be modified in such a way that they can be used in all hitherto disclosed types of liquid crystal display elements.

Such additives are known to those skilled in the art and are extensively described in the literature. For example, it is possible to add conducting salts, preferably ethyldimethyldodecylammonium 4-hexyloxybenzoate, tetrabutylammonium tetraphenylboranate or complex salts of crown ethers (cf. for example I. Haller et al., Mol. Cryst. Liq. Cryst. Volume 24, pages 249–258 (1973)) to improve the conductivity, dichroic dyes for producing coloured guest-host systems or substances to alter the dielectric anisotropy, the viscosity and/or the orientation of the nematic phases. Such substances are described for example in German Offenlegungsschriften Nos. 2,209,127, 2,240,864, 2,321,632, 2,338,281, 2,450,088, 2,637,430, 2,853,728 and 2,902,177.

The following examples serve to illustrate the invention without limiting it. Heretofore and hereinafter percentages are by weight. All temperatures are given in degrees celsius.

EXAMPLE 1

A solution of 12.2 g of trans-4-(4-aminocyclohexyl)-butylcyclohexane in 135 ml of dichloromethane is added dropwise at 0° under nitrogen to a solution of 15.2 g of 1,1'-thiocarbonyldiimidazole in 90 ml of dichloromethane in the course of 1.5 hours. After standing overnight, about 140 ml of 3% hydrochloric acid are added at 0°–4° until pH 2 is obtained. The organic phase separated off is washed with water until pH 6, is dried over sodium sulfate and evaporated. Purification of the crude product (15.6 g) by column chromatography leaves 13.1 g of trans-4-(4-isothiocyanatocyclohexyl)-butylcyclohexane. Melting point (m.p.) +23°; clear point (c.p.) +72.9°.

Prepared analogously: trans-4-(4-isothiocyanatocyclohexyl)-ethylcyclohexane trans-4-(4-isothiocyanatocyclohexyl)-propylcyclohexane
m.p. +39°, c.p. +77.5° trans-4-(4-isothiocyanatocyclohexyl)-butylcyclohexane trans-4-(4-isothiocyanatocyclohexyl)-pentylcyclohexane trans-4-(4-isothiocyanatocyclohexyl)-hexylcyclohexane trans-4-(4-isothiocyanatocyclohexyl)-octylcyclohexane trans-4-(4-isothiocyanatocyclohexyl)-decylcyclohexane

EXAMPLE 2

38.3 g of 4-(4-aminocyclohexyl)-4'-(4-pentylcyclohexyl)-biphenyl (obtained from 4,4'-bis(4-oxocyclohexyl)biphenyl by monoaddition of amylmagnesium bromide, dehydration of the tertiary alcohol and catalytic hydrogenation to 4-(4-pentylcyclohexyl)-4'-(4-oxocyclohexyl)biphenyl, conversion of the latter into the oxime and hydride reduction) are dissolved in 450 ml of dichloromethane and 15 ml of triethylamine, and 12 g of thiophosgene are slowly added at room temperature. After all the thiophosgene has been added the reaction mixture is stirred for a further 12 hours.

Working-up comprises washing with water and freeing the organic phase of solvent. The residue is crystallized from ethanol to give 4-(4-isothiocyanatocyclohexyl)4'-(pentylcyclohexyl)-biphenyl.

Prepared analogously:
4-(4-isothiocyanatocyclohexyl)-4'-(4-propylcyclohexyl)biphenyl
4-(4-isothiocyanatocyclohexyl)-4'-(4-butylcyclohexyl)-biphenyl
4-(4-isothiocyanatocyclohexyl)-4'-(4-hexylcyclohexyl)-biphenyl
4-(4-isothiocyanatocyclohexyl)-4'-(4-heptylcyclohexyl)biphenyl
4-(4-isothiocyanatocyclohexyl)-4'-(4-octylcyclohexyl)-biphenyl
4-(4-isothiocyanatocyclohexyl)-4'-(4-decylcyclohexyl)-biphenyl

EXAMPLE 3

48.6 g of 4-amino-4'-(4-propylcyclohexyl)biphenyl (obtained from 4-(4-propylcyclohexyl)-biphenyl by bromination and reacting the corresponding 4-bromobiphenyl with ammonia/water at 200° in the presence of Cu/CuCl) are stirred at 0° for 30 hours together with 10 g of carbon disulfide and 30 ml of triethylamine in 650 ml of toluene. Thereafter the precipitated mass of triethylammonium dithiocarbamate crystals is filtered off and washed with toluene.

The intermediate is suspended in a mixture of 500 ml of chloroform and 50 ml of triethylamine. Ethyl chlorocarbonate (21 g) is then added dropwise.

To remove excess triethylamine, dilute hydrochloric acid is used for washing and the solvents are evaporated off under reduced pressure. Crystallization of the residue gives 4-isothiocyanato-4'-(4-propylcyclohexyl)-biphenyl; m.p. 149.3°, c.p. 240.5°.

Obtained analogously:
4-isothiocyanato-4'-(4-butylcyclohexyl)-biphenyl;
m.p. 119.8°, c.p. 233.0°
4-isothiocyanato-4'-(4-pentylcyclohexyl)-biphenyl;
m.p. 123.0°, c.p. 233.5°
4-isothiocyanato-4'-(4-hexylcyclohexyl)-biphenyl;

m.p. 96.2°, c.p. 223.0°
4-isothiocyanato-4'-(4-heptylcyclohexyl)-biphenyl; m.p. 108.8°, c.p. 219.5°
4-isothiocyanato-4'-(4-octylcyclohexyl)-biphenyl
4-isothiocyanato-4'-(4-decylcyclohexyl)-biphenyl
4-isothiocyanato-4'-(4-dodecylcyclohexyl)-biphenyl

EXAMPLE 4

29.1 g of 4-(4-(4-pentylcyclohexyl)cyclohexyl)aniline (obtained from 4-(4-(4-pentylcyclohexyl)-cyclohexyl)-benzene analogously to the preparation of 4-amino-'-(4-propylcyclohexyl)biphenyl) are converted with carbon disulfide and ethyl chlorocarbonate and intermediate isolation of the triethylammonium dithiocarbamate into the corresponding mustard oil.

Crystallization of the crude product gives 4-(4-(4-pentylcyclohexyl)-cyclohexyl)-phenyl isothiocyanate.
Obtained correspondingly:
4-(4-(4-ethylcyclohexyl)-cyclohexyl)-phenyl isothiocyanate
4-(4-(4-propylcyclohexyl)-cyclohexyl)-phenyl isothiocyanate
4-(4-(4-butylcyclohexyl)-cyclohexyl)-phenyl isothiocyanate
4-(4-(4-hexylcyclohexyl)-cyclohexyl)-phenyl isothiocyanate
4-(4-(4-heptylcyclohexyl)-cyclohexyl)-phenyl isothiocyanate
4-(4-(4-octylcyclohexyl)-cyclohexyl)-phenyl isothiocyanate
4-(4-(4-nonylcyclohexyl)-cyclohexyl)-phenyl isothiocyanate
4-(4-(4-undecylcyclohexyl)-cyclohexyl)-phenyl isothiocyanate

EXAMPLE 5

32.5 g of 4-(4-(4-butylcyclohexylethyl)-cyclohexyl)-aniline (obtainable from 4-(4-(4-butylcyclohexylethyl)-cyclohexyl)-benzene by bromination and ammonolysis as described in Example 2) are converted with 12 g of thiophosgene in the presence of 20 ml of triethylamine into the corresponding dithiocarbamate as described in Example 3.

The salt is added to 150 ml of 30% hydrogen peroxide solution a little at a time, and the mixture is subsequently stirred at 40° for 2 hours. After cooling down the precipitated product is filtered off with suction. Crystallization from toluene gives 4-(4(4-butylcyclohexylethyl)-cyclohexyl)-phenyl mustard oil.

Obtained analogously:
4-(4-(4-propylcyclohexylethyl)-cyclohexyl)-phenyl isothiocyanate
4-(4-(4-pentylcyclohexylethyl)-cyclohexyl)-phenyl isothiocyanate
4-(4-(4-heptylcyclohexylethyl)-cyclohexyl)-phenyl isothiocyanate
4-(4-(4-octylcyclohexylethyl)-cyclohexyl)-phenyl isothiocyanate
4-(4-(4-nonylcyclohexylethyl)-cyclohexyl)-phenyl isothiocyanate
4-(4-(4-undecylcyclohexylethyl)-cyclohexyl)-phenyl isothiocyanate
4-(4-(4-tridecylcyclohexylethyl)-cyclohexyl)-phenyl isothiocyanate

EXAMPLE 6

27.7 g of 2-fluoro-4-(4-heptylcyclohexyl)-aniline (obtainable from 2-fluoro-4-bromonitrobenzene by lithiation at −100° and reaction with 4-heptylcyclohexanone, dehydration of the tertiary alcohol and reduction of double bond and nitro group).are stirred for 24 hours at room temperature in 300 ml of chloroform together with 12 g of thiophosgene and 25 ml of triethylamine. This is followed by washing with water and concentrating the organic phase after drying, to give 2-fluoro-4-(4-heptylcyclohexyl)-phenyl mustard oil.

Obtained analogously:
2-fluoro-4-(4-propylcyclohexyl)-phenyl isothiocyanate
2-fluoro-4-(4-butylcyclohexyl)-phenyl isothiocyanate
2-fluoro-4-(4-pentylcyclohexyl)-phenyl isothiocyanate
2-fluoro-4-(4-nonylcyclohexyl)-phenyl isothiocyanate
2-fluoro-4-(4-decylcyclohexyl)-phenyl isothiocyanate
2-fluoro-4-(4-dodecylcyclohexyl)-phenyl isothiocyanate

EXAMPLE 7

2-(4-Aminophenyl)-5-pentylpyrimidine (prepared from 4-aminophenylamidine and 2-pentylpropane-1,3-diol) is reacted with thiophosgene as described in Example 3, affording 2-(4-isothiocyanatophenyl)-5-pentylpyrimidine; m.p. 46°, c.p. 85.5°.

Obtained correspondingly:
24-isothiocyanatophenyl)-5-ethylpyrimidine
24-isothiocyanatophenyl)-5-propylpyrimidine
24-isothiocyanatophenyl)-5-butylpyrimidine; m.p. 60.8°, c.p. 77.8 °
24-isothiocyanatophenyl)-5-hexylpyrimidine
24-isothiocyanatophenyl)-5-heptylpyrimidine
24-isothiocyanatophenyl)-5-octylpyrimidine
24-isothiocyanatophenyl)-5-nonylpyrimidine
24-isothiocyanatophenyl)-5-decylpyrimidine
24-isothiocyanatophenyl)-5-undecylpyrimidine
24-isothiocyanatophenyl)-5-dodecylpyrimidine
24-isothiocyanatophenyl)-5-tridecylpyrimidine

EXAMPLE 8

3-Fluoro-4-aminophenyl 4-propylcyclohexanecarboxylate (obtainable from 4-propylcyclohexanecarboxylic acid and 3-fluoro-4-nitrophenol by means of dicyclohexylcarbodiimide in dichloromethane and subsequent reduction of the nitro group with sodium dithionite) is converted as described in Example 6 to 3-fluoro-4-isothiocyanatophenyl 4-propylcyclohexanecarboxylate.

Obtained analogously:
3-fluoro-4-isothiocyanatophenyl 4-butylcyclohexanecarboxylate
3-fluoro-4-isothiocyanatophenyl 4-pentylcyclohexanecarboxylate
3-fluoro-4-isothiocyanatophenyl 4-hexylcyclohexanecarboxylate
3-fluoro-4-isothiocyanatophenyl 4-heptylcyclohexanecarboxylate
3-fluoro-4-isothiocyanatophenyl 4-octylcyclohexanecarboxylate
3-fluoro-4-isothiocyanatophenyl 4-nonylcyclohexanecarboxylate
3-fluoro-4-isothiocyanatophenyl 4-decylcyclohexanecarboxylate
3-fluoro-4-isothiocyanatophenyl 4-dodecylcyclohexanecarboxylate

EXAMPLE 9

4-Aminophenyl 4-(4-hexylcyclohexylethyl)-cyclohexanecarboxylate (prepared from 4-(4-hexylcyclohexylethyl)-cyclohexanecarboxylic acid and 4-nitrophenol by means of dicyclohexylcarbodiimide and subsequent catalytic reduction of the nitro group) is converted as described in Example 6 to 4-isothiocyanatophenyl 4-(4-hexylcyclohexylethyl)-cyclohexanecarboxylate.

Obtained in the same way:
4-isothiocyanatophenyl 4-(4-propylcyclohexylethyl)cyclohexanecarboxylate
4-isothiocyanatophenyl 4-(4-butylcyclohexylethyl)cyclohexanecarboxylate
4-isothiocyanatophenyl 4-(4-pentylcyclohexylethyl)cyclohexanecarboxylate
4-isothiocyanatophenyl 4-(4-heptylcyclohexylethyl)cyclohexanecarboxylate
4-isothiocyanatophenyl 4-(4-octylcyclohexylethyl)cyclohexanecarboxylate
4-isothiocyanatophenyl 4-(4-nonylcyclohexylethyl)cyclohexanecarboxylate
4-isothiocyanatophenyl 4-(4-decylcyclohexylethyl)cyclohexanecarboxylate
4-isothiocyanatophenyl 4-(4-undecylcyclohexylethyl)-cyclohexanecarboxylate
4-isothiocyanatophenyl 4-(4-dodecylcyclohexylethyl)-cyclohexanecarboxylate

EXAMPLE 10

26.8 g of 2-(4-aminophenyl)-5-heptylpyridine (prepared from 5-heptyl-2-phenylpyridine by acylation and conversion of the 2-(4-acetylphenyl)-5-heptylpyridine into the corresponding oxime, Beckmann rearrangement thereof by means of phosphorus trichloride/pyridine and hydrolysis of 2-(4-acetamidophenyl)-5-heptylpyridine) are reacted with carbon disulfide and ethyl chlorocarbonate as described in Example 3.

The crystallization of the crude product gives 4-(5-heptylpyridin-2-yl)-phenyl isothiocyanate.

Obtained correspondingly:
4-(5-ethylpyridin-2-yl)-phenyl isothiocyanate
4-(5-propylpyridin-2-yl)-phenyl isothiocyanate
4-(5-butylpyridin-2-yl)-phenyl isothiocyanate
4-(5-hexylpyridin-2-yl)-phenyl isothiocyanate
4-(5-octylpyridin-2-yl)-phenyl isothiocyanate
4-(5-nonylpyridin-2-yl)-phenyl isothiocyanate
4-(5-undecylpyridin-2-yl)-phenyl isothiocyanate
4-(5-(4-ethylcyclohexyl)-pyridin-2-yl)-phenyl isothiocyanate
4-(5-(4-propylcyclohexyl)-pyridin-2-yl)-phenyl isothiocyanate
4-(5-(4-butylcyclohexyl)-pyridin-2-yl)-phenyl isothiocyanate
4-(5-(4-hexylcyclohexyl)-pyridin-2-yl)-phenyl isothiocyanate
4-(5-(4-heptylcyclohexyl)-pyridin-2-yl)-phenyl isothiocyanate
4-(5-(4-octylcyclohexyl)-pyridin-2-yl)-phenyl isothiocyanate
4-(5-(4-nonylcyclohexyl)-pyridin-2-yl)-phenyl isothiocyanate
4-(5-(4-undecylcyclohexyl)-pyridin-2-yl)-phenyl isothiocyanate
4-(5-(4-ethylphenyl)-pyridin-2-yl)-phenyl isothiocyanate
4-(5-(4-propylphenyl)-pyridin-2-yl)-phenyl isothiocyanate
4-(5-(4-butylphenyl)-pyridin-2-yl)-phenyl isothiocyanate
4-(5-(4-hexylphenyl)-pyridin-2-yl)-phenyl isothiocyanate
4-(5-(4-heptylphenyl)-pyridin-2-yl)-phenyl isothiocyanate
4-(5-(4-octylphenyl)-pyridin-2-yl)-phenyl isothiocyanate
4-(5-(4-nonylphenyl)-pyridin-2-yl)-phenyl isothiocyanate
4-(5-(4-undecylphenyl)-pyridin-2-yl)-phenyl isothiocyanate

EXAMPLE 11

39.4 g of 4-(4-(4-(4-pentylcyclohexyl)-cyclohexyl)-cyclohexyl)-aniline (prepared from (4-(4-(4-cyclohexyl)-cyclohexyl)-cyclohexyl)-benzene analogously to the method indicated in Example 10) are converted with thiophosgene and triethylamine into the corresponding dithiocarbamate.

Reaction with 30% hydrogen peroxide solution and crystallization of the crude product gives 4-(4-(4-(4-pentylcyclohexyl)-cyclohexyl)-cyclohexyl)-phenyl isothiocyanate.

Obtained analogously:
4-(4-(4-(4-ethylcyclohexyl)-cyclohexyl)-cyclohexyl)-phenyl isothiocyanate
4-(4-(4-(4-propylcyclohexyl)-cyclohexyl)-cyclohexyl)-phenyl isothiocyanate
4-(4-(4-(4-butylcyclohexyl)-cyclohexyl)-cyclohexyl)-phenyl isothiocyanate
4-(4-(4-(4-hexylcyclohexyl)-cyclohexyl)-cyclohexyl)-phenyl isothiocyanate
4-(4-(4-(4-heptylcyclohexyl)-cyclohexyl)-cyclohexyl)-phenyl isothiocyanate
4-(4-(4-(4-octylcyclohexyl)-cyclohexyl)-cyclohexyl)-phenyl isothiocyanate
4-(4-(4-(4-nonylcyclohexyl)-cyclohexyl)-cyclohexyl)-phenyl isothiocyanate
4-(4-(4-(4-undecylcyclohexyl)-cyclohexyl)-cyclohexyl)phenyl isothiocyanate

EXAMPLE 12

38.3 g of 1-(4-(4-propylcyclohexyl)-cyclohexyl)2-(4-aminophenyl)-ethane (obtained from (2-(4-(4-propylcyclohexyl)-cyclohexyl)-ethyl)-benzene analogously to the method indicated in Example 10) are reacted with 1,1′thiocarbonyldiimidazole in dichloromethane in accordance with the method used in Example 1.

Crystallization of the crude product gives 1-(4-(4-propylcyclohexyl)-2-(4-isothiocyanatophenyl)-ethane; m.p. 43.0°, c.p. 38.6°.

Obtained analogously:
1-(4-(4-ethylcyclohexyl)-2-(4-isothiocyanatophenyl)ethane
1-(4-(4-butylcyclohexyl)-2-(4-isothiocyanatophenyl)ethane; m.p. 23.5°, c.p. 33,6°
1-(4-(4-pentylcyclohexyl)-2-(4-isothiocyanatophenyl)ethane; m.p. 41.0°, c.p. 47.5°
1-(4-(4-hexylcyclohexyl)-2-(4-isothiocyanatophenyl)ethane; m.p. 50.0°, c.p. 41.4°
1-(4-(4-heptylcyclohexyl)-2-(4-isothiocyanatophenyl)ethane; m.p. 56.2°, c.p. 49.2°
1-(4-(4-octylcyclohexyl)-2-(4-isothiocyanatophenyl)ethane;
1-(4-(4-nonylcyclohexyl)-2-(4-isothiocyanatophenyl)ethane;
1-(4-(4-undecylcyclohexyl)-2-(4-isothiocyanatophenyl)ethane

EXAMPLE 13

76.6 g of 1-(4-heptylcyclohexyl)-2-(4-(4-aminophenyl)-cyclohexyl)-ethane (prepared from 1-(heptylcyclohexyl)-2-(4-phenylcyclohexyl)-ethane analogously to the method indicated in Example 10) are converted with thiophosgene and triethylamine into the corresponding dithiocarbamate.

Reaction with 30% hydrogen peroxide solution and crystallization of the crude product gives 1-(4-heptylcyclohexyl)-2-(4-(4-isothiocyanatophenyl)-cyclohexyl)ethane.

Obtained analogously:
1-(4-propylcyclohexyl)-2-(4-(4-isothiocyanatophenyl)-cyclohexyl)-ethane
1-(4-butylcyclohexyl)-2-(4-(4-isothiocyanatophenyl)-cyclohexyl)-ethane
1-(4-pentylcyclohexyl)-2-(4-(4-isothiocyanatophenyl)-cyclohexyl)-ethane
1-(4-hexylcyclohexyl)-2-(4-(4-isothiocyanatophenyl)-cyclohexyl)-ethane
1-(4-octylcyclohexyl)-2-(4-(4-isothiocyanatophenyl)-cyclohexyl)-ethane
1-(4-nonylcyclohexyl)-2-(4-(4-isothiocyanatophenyl)-cyclohexyl)-ethane
1-(4-decylcyclohexyl)-2-(4-(4-isothiocyanatophenyl)-cyclohexyl)-ethane
1-(4-undecylcyclohexyl)-2-(4-(4-isothiocyanatophenyl)-cyclohexyl)-ethane
1-(4-dodecylcyclohexyl)-2-(4-(4-isothiocyanatophenyl)-cyclohexyl)-ethane

We claim:

1. A mustard oil of the formula I $$R-(A^1-Z^1)_n-A^2-Z^2-A^3-NCS \quad (I)$$

in which
R is H or alkyl of 1-15 C atoms, in which one or two non-adjacent $CH_2$ groups can be replaced by $-O-$, $-CO-$, $-O-CO-$ and/or $-CO-O-$
$A^1$ and $A^2$ are each an unsubstituted or monosubstituted or polysubstituted 1,4-cyclohexylene group, a piperidine-1,4-diyl or 1,4-bicyclo[2,2,2]octylene group or a 1,4-phenylene group which is unsubstituted or substituted by one or two F and/or Cl atoms and/or $CH_3$ groups and/or CN groups and in which one or two CH groups can also be replaced by N,
$A^3$ is a 1,4-cyclohexylene group or a 1,4-phenylene group which is unsubstituted or substituted by one F atom,
$Z^1$ and $Z^2$ are each $-CO-O-$, $-O-CO-$, $-CH_2CH_2-$, $CHCN-CH_2-$, $-CH_2-CHCN-$, $-CH=CH-$, $-OCH_2-$, $-CH_2O-$, $-CH=N-$, $-N=CH-$, $-NO=N-$, $-N=NO-$ or a single bond,
n is 0, 1 or 2,
Cy is 1,4-cyclohexylene and
Phe is 1,4-phenylene.

2. A liquid crystalline phase having at least two liquid-crystalline components, wherein at least one 3. A liquid crystal display element, comprising a liquid-crystalline phase wherein said phase is one of claim 2.

4. An electro-optical display element, comprising a liquid-crystalline dielectric, wherein said dielectric is a phase according to claim 2.

5. A mustard oil of claim 1 of the following formulae

| R—Cy—Cy—NCS | I1 |
| R—Cy—Phe—Cy—NCS | I5 |
| R—Cy—Phe—Phe—Cy—NCS | I13 |
| R—Cy—PheF—Phe—Cy—NCS | I14 | in which R, Cy and Phe are as defined in claim 1, and PheF is a 1,4-phenylene group substituted by fluorine in the 2- or 3-position.

6. A mustard oil of claim 1 of the formula

Alkyl—Cy—Cy—NCS, or

Oxaalkyl—Cy—Cy—NCS in which Cy is as defined in claim 1, and alkyl is methyl, ethyl, propyl, butyl, pentyl, hexyl, heptyl, octyl, nonyl or decyl, and
oxaalkyl is 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

7. A mustard oil of claim 1 of the formula

Alkyl—Cy—Phe—Cy—NCS in which Cy and Phe are as defined in claim 1 and alkyl is methyl, ethyl, propyl, butyl, pentyl, hexyl, heptyl, octyl, nonyl or decyl.

8. A mustard oil of claim 1 of the formula

Alkoxycarbonyl—Cy—$CH_2CH_2$—Cy—(Phe—2F)—NCS or

Alkoxycarbonyl—Cy—$CH_2CH_2$—Cy—(Phe—3F)—NCS in which Cy and Phe are as defined in claim 1,
alkoxycarbonyl is methoxy-, ethoxy-, propoxy-, butoxy-, pentoxy-, hexoxy-, heptoxy- or octoxycarbonyl,
Phe-2F is a 1,4-phenylene group substituted by fluorine in the 2-position and
Phe-3F is a 1,4-phenylene group substituted by fluorine in the 3-position.

9. A mustard oil of claim 1 of the formula

Alkyl—Pym—(Phe—2F)—NCS,

Alkyl—Pym—(Phe—3F)—NCS,

Alkoxycarbonyl—Pym—(Phe—2F)—NCS, or

Alkoxycarbonyl—Pym—(Phe—3F)—NCS, in which
alkyl is methyl, ethyl, propyl, butyl, pentyl, hexyl, heptyl, octyl, nonyl or decyl, alkoxycarbonyl is methoxy-, ethoxy-, propoxy-, butoxy-, pentoxy-, hexoxy-, heptoxy- or octoxycarbonyl,
Phe-2F is a 1,4-phenylene group substituted by fluorine in the 2-position,
Phe-3F is a 1,4-phenylene group substituted by fluorine in the 3-position, and
Pym is a pyrimidine-2,5-diyl group.

10. A mustard oil of claim 1 of the formula

Alkyl—Cy—COO—(Phe—2F)—NCS, or

Alkyl—Cy—COO—(Phe—3F)—NCS in which Cy is as defined in claim 1,
alkyl is methyl, ethyl, propyl, butyl, pentyl, hexyl, heptyl, octyl, nonyl or decyl,
Phe-2F is a 1,4-phenylene group substituted by fluorine in the 2-position, and
Phe-3F is a 1,4-phenylene group substituted by fluorine in the 3-position.

11. A mustard oil of claim 1 of the formula

Alkyl—Cy—Phe—Phe—Cy—NCS

Alkyl—Cy—(Phe—2F)—Cy—NCS, or

Alkyl—Cy—(Phe—3F)—Cy—NCS in which Cy and Phe are as defined in claim 1,
alkyl is methyl, ethyl, propyl, butyl, pentyl, hexyl, heptyl, octyl, nonyl or decyl,
Phe-2F is a 1,4-phenylene group substituted by fluorine in the 2-position, and
Phe-3F is a 1,4-phenylene group substituted by fluorine in the 3-position.

* * * * *